United States Patent [19]

Hon et al.

[11] Patent Number: 5,025,792
[45] Date of Patent: Jun. 25, 1991

[54] CONTINUOUS CUTANEOUS BLOOD PRESSURE MEASURING APPARATUS AND METHOD

[75] Inventors: Edward H. Hon; Edward D. Hon, both of Bradbury, Calif.

[73] Assignee: The Hon Group, Encino, Calif.

[21] Appl. No.: 780,398

[22] Filed: Sep. 26, 1985

[51] Int. Cl.⁵ ............................................ A61B 5/021
[52] U.S. Cl. ...................................... 128/672; 128/690
[58] Field of Search ............... 128/672, 675, 677, 686, 128/687, 667, 691, 694

[56] References Cited

U.S. PATENT DOCUMENTS

| | | | |
|---|---|---|---|
| 2,753,863 | 7/1956 | Bailey | 128/686 X |
| 3,154,067 | 10/1964 | Stenstrom et al. | 128/687 |
| 3,299,882 | 1/1967 | Masino | 128/687 X |
| 3,545,430 | 12/1970 | Figar | 128/694 |
| 3,570,474 | 3/1971 | Jonson | 128/694 |
| 3,704,708 | 12/1972 | Iberall | 128/686 X |
| 4,202,347 | 5/1980 | Sacks | 128/677 |
| 4,331,155 | 5/1982 | Sacks | 128/686 |
| 4,429,700 | 2/1984 | Thees et al. | 128/686 X |
| 4,432,374 | 2/1984 | Osanai | 128/694 |
| 4,441,504 | 4/1984 | Peterson et al. | 128/686 |
| 4,524,777 | 6/1985 | Kisioka et al. | 128/694 X |

FOREIGN PATENT DOCUMENTS 2394282 2/1979 France .................... 128/677

*Primary Examiner*—Angela D. Sykes
*Attorney, Agent, or Firm*—Lewis Anten

[57] ABSTRACT

Apparatus and method for continuously measuring cutaneous blood pressure is disclosed. A portion of cutaneous tissue, preferably covering a digit such as a finger, is isolated and a pressure sensing device, such as a strain gauge, measures the changes in pressure in the isolated cutaneous tissue. The pressure sensing device is mounted on a stable platform fixed relative to the cutaneous tissue of the digit.

15 Claims, 5 Drawing Sheets

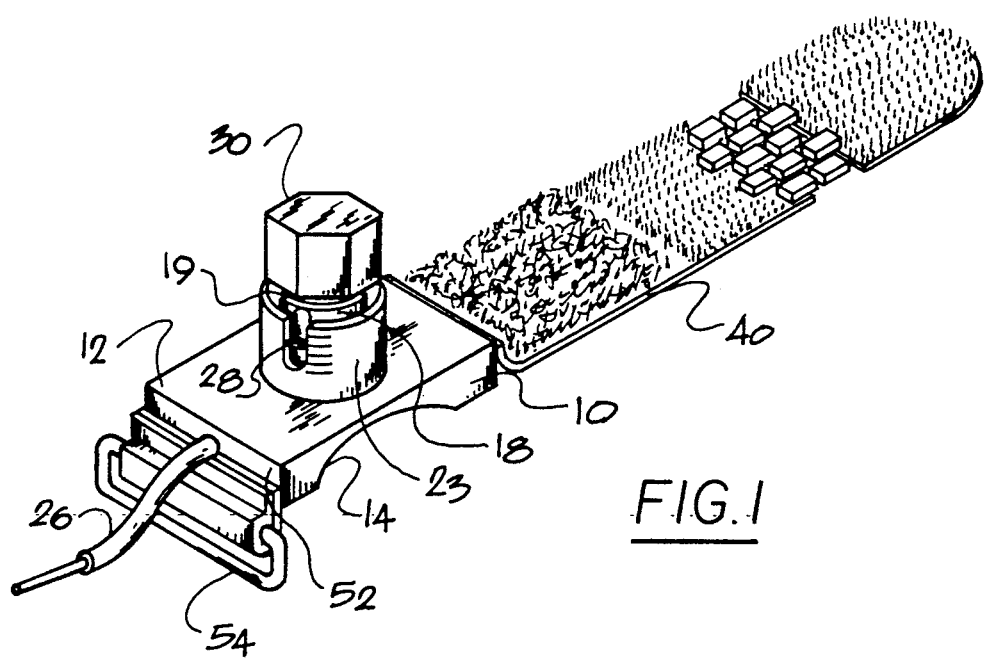
FIG. 1
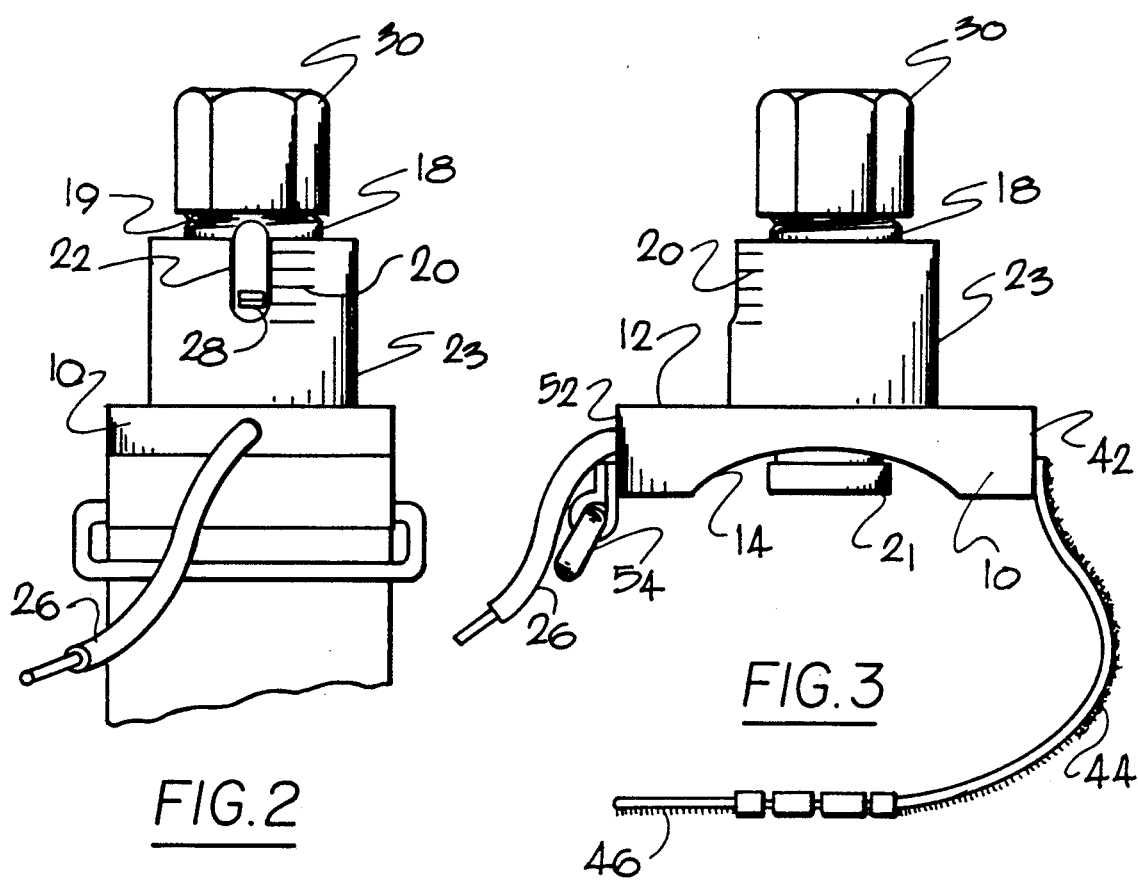
FIG. 2
FIG. 3

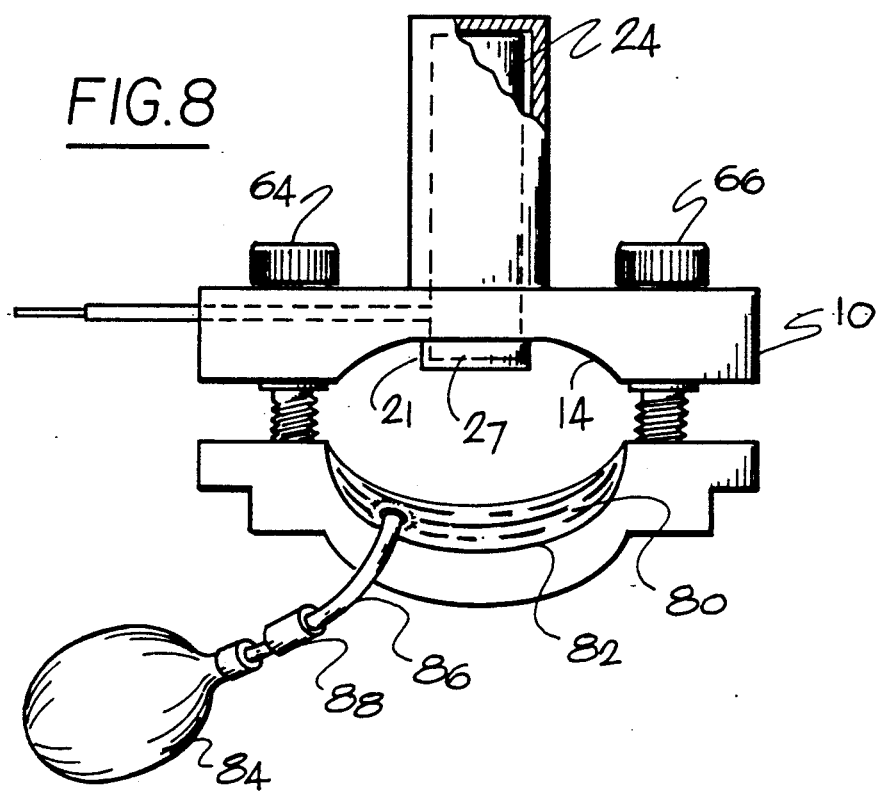
FIG.8
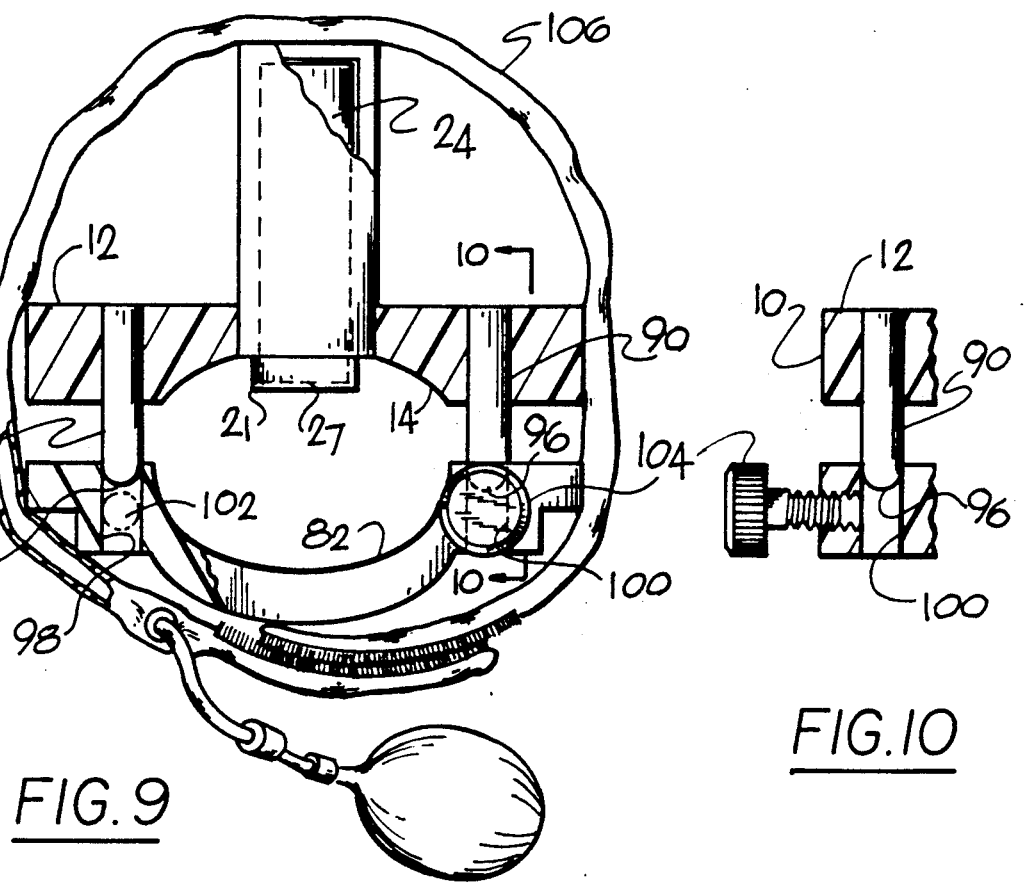
FIG.9
FIG.10

CONTINUOUS CUTANEOUS BLOOD PRESSURE MEASURING APPARATUS AND METHOD

BACKGROUND OF THE INVENTION

This invention relates to a method and apparatus for continuously and non-invasively measuring cutaneous blood pressure in a small isolated flesh element. The physiological data thus obtained are related to, but not identical, to blood pressure measurements of a more central arterial circulation, such as that obtained with the conventional auscultatory method of estimating brachial blood pressure.

In particular, the invention finds use as part of a general system for measurement of blood pressure based on repetitive evaluation of the cutaneous pressure fluctuation patterns of minute branches of larger arteries and therefore reflects the arterial blood pressure of the general circulation. This is to be expected since the latter is the source of the former.

The method and apparatus of the present invention enables continuous monitoring of blood pressure patterns over extended periods of time. This is needed in the evaluation of circulatory function and ambulatory monitoring of cardiac function, and is useful for hypertension studies and for obtaining records of circulation in the peripheral systems, particularly of the limbs, fingers and toes.

In the past, various artery occlusion procedures have been used stopping blood flow in radial, brachial, dorsalis pedis, temporal and other arteries to estimate blood pressure, particularly of the central circulatory system. Data thus obtained is by its very nature discontinous.

It has been possible to insert pressure sensing devices and/or catheters temporarily into the arteries of the circulatory system for direct continuous measurements (invasive method of measuring). While intra-arterial catheterization may provide more precise measurements of blood pressure than arterial occlusion devices, the pressure measured is likely to be more related to the central circulation, than the peripheral circulation. Also, the blood pressure measurements and patterns thus obtained are likely to be altered by the traumatic operation of inserting the catheter, by the drug administered so that the catheter can be inserted, and by the presence of a foreign body in the circulatory system.

The principal non-invasive blood pressure measuring device used today is an auscultatory system where a pressure is applied to occlude a major artery, such as the brachial artery. In practice, an inflatable encircling cuff is placed around the arm and inflated to occlude the major artery, e.g., brachial, to prevent flow of blood in the artery. As the pressure in the cuff is slowly lowered, permitting flow of blood in the artery, Korotkoff sounds are heard. The cuff pressure at which the first sound is heard is defined as the systolic pressure. The pressure in the cuff is then lowered further the pressure in the cuff at which the sound fades is defined as the diastolic pressure.

A second occluding cuff technique uses palpation of the pulse rather than auscultation. In this palpatory system, as the occluding cuff pressure is slowly released, arterial pulsations are detected by palpation. The pressure level of the cuff at which the pulsations are first perceived is designated as systolic blood pressure. Diastolic blood pressure cannot be detected by palpation.

Another occluding cuff system uses the maximum and minimum oscillations of arterial blood pressure as referenced to cuff pressure as indications of systolic and diastolic blood pressure, respectively. In addition to being an intermittent, occlusive technique, the measurements thus obtained are likely influenced by the limb volume of the limb around which the cuff is applied.

It can be generally stated that all blood pressure measurements which are based upon arterial occlusion are inherently discontinuous, needing to be repeated, at best, from time to time. Such measurements cannot resolve blood pressure patterns on a beat to beat basis, or show the wave form of the individual beats.

Thus, although the current method of auscultatory measurement of brachial blood pressure is by far the most widely used technique for blood pressure measurement, the technique is relatively imprecise, since the observed values vary from observer to observer and the very act of taking blood pressure itself causes a momentary change in blood pressure. Additionally, since the occlusion itself is known to have physiological and psychological effects, the measurements may be distorted.

A non-invasive, non-occlusive approach to the measurement of blood pressure would have many advantages. Unfortunately, prior techniques for this purpose have been found to have disadvantages. Those directed at measuring arterial pressure by placing a transducer directly over a partially compressed radial or dorsalis pedis artery can, under optimum circumstances, provide accurate records for short periods of time. However, the required counter pressure has to be maintained, e.g. with a pneumatic system, and considerable difficulty is experienced in maintaining constant mechanical coupling between the tissue overlying the artery and pressure on the arterial wall during even the slightest patient motion.

An example of this type of measuring system is disclosed in U.S. Pat. No. 3,880,145 to E. F. Blick, issued Apr. 29, 1975. Blick described a system using a strain gauge to flatten the radial artery at the inside of the wrist. A second sensor is mounted cutaneously alongside but off the artery. The signal from the second sensor was subtracted from that sensor associated with the flattened artery. In practice, the signal from the radial artery sensor contains arterial pulsations as well as "noise". The noise which is measured by the cutaneous transducer is subtraced from the former signal, leaving a measurement of the arterial pulsations alone. Such systems are complex and during patient movement it is very difficult to precisely match the "noise" component arising from both sensors.

In the prior devices discussed above, the majority are directed to the measurment of blood pressure in major arteries Elastic strain gauge techniques which encircle limbs or digits have also been used. In such devices, a finger or toe is encircled with a latex or silastic tube which contains mercury. As the digit volume increases with arterial inflow and decreases with venous outflow, the change in volume can be measured and related to blood pressure. However, the system is occlusive in nature and markedly decreases capillary blood flow. Hence, again it can be used only intermittently since it causes distortion of the physiological data. It is not possible to obtain continuous blood pressure records for hours at a time. It is difficult to calibrate since it is temperature sensitive, and must be calibrated off of the body part.

Hand and thumb plethysmographs are also known which measure changes in volume of entire digits, hands, feet, or limbs, but they are very cumbersome and cannot be used on an active patient, such as one jogging.

A general discussion and review of various previously proposed systems for blood pressure monitoring is given in the book, "The Direct and Indirect Measurement of Blood Pressure," by L. A. Geddes (Year Book Medical Publishers, Chicago, 1970) where a number of blood pressure techniques are outlined (see pages 37, 71, 87 and 96).

It has been demonstrated that there is a hitherto unfulfilled need for a sensitive, continuous, non-invasive, non-occlusive measuring technique for recording blood pressure measurements and beat to beat patterns undistorted and uninterrupted by the measuring system, per se. The method and the apparatus of the present invention enables non-invasive, non-occlusive continuous measurements over extended periods of time. Continuous information of this type is essential for adequate evaluation of cardiac and vascular function. It is of particular importance in the diagnosis and treatment of hypertension, since it provides detailed information concerning the peripheral circulation not available heretofore.

SUMMARY OF THE INVENTION

The apparatus of the present invention continuously measures cutaneous blood pressure with a strain gauge (or similar pressure measuring device) attached to a portion of the body, preferably on the fleshy part of the thumb.

A major use of the apparatus is to provide continuous blood pressure measurements and patterns of blood pressure in the fingers and toes. To maintain mechanical stability of the platform the encircling means must be closely applied to a relatively hard stable reference point e.g. such as the bone at the back of the thumb which is covered with a small portion of cutaneous tissue. Since the blood supply to the digits course along their lateral aspects there is no appreciable diminution in the overall blood supply to the digits by the attachment of the platform to the digit.

A small portion of cutaneous tissue is isolated from the surrounding tissue by a ring depending from the strain gauge or the platform and pressing against the thumb. This ring projects beyond the measuring surface of the strain gauge and serves to reduce noise emanating from adjacent tissue and isolates the cutaneous tissue.

The blood pressure in this protruding isolated cutaneous tissue is measured with a cylindrical strain gauge (or other pressure measuring device) whose measuring surface is tangentially oriented to the slightly domed segregated cutaneous tissue. The isolating ring essentially surrounds the circumference of the bottom of the strain gauge. The long axis of the strain gauge is normal to the upper surface of the stabilizing platform.

Together, the ring and lower portion of the strain gauge form an inverted shallow dish in which the inside circumference of the ring forms the peripheral walls and the bottom measuring surface of the strain gauge its bottom. Consequently, when the strain gauge assembly is pressed against the isolated cutaneous tissue, its superficial layers fill the space between the ring and the strain gauge measuring surface. The minute blood pressure changes in this portion of the cutaneous tissue are detected by the strain gauge and can be observed on an oscilloscope or recorded in a conventional manner, such as on a strip chart or magnetic tape.

The magnitude of the recorded blood pressure changes are affected not only by the change within the isolated cutaneous tissue, but also by the forces which are holding the ring against the tissue. In order to keep these forces sufficiently constant, the strain gauge assembly must be attached to the stabilizing platform in a substantially rigid, mechanical manner. This is done with a rigid cap screw mounted to a sleeve surrounding the gauge. Appropriate pressure is achieved by a spring fitted between the inside surface of the cap and the strain gauge assembly.

In practice, the initial ring pressure may be adjusted so that the observed cutaneous blood pressure is a given number of mms Hg. below the brachial systolic blood pressure, if the latter is used as a reference point. Alternatively, a predetermined known coupling pressure may be applied to the non-active end of the strain gauge assembly by mechanical means, such as a calibrated spring, by pneumatic means, or directly by a rigid rod where the coupling pressure is measured by another strain gauge or other pressure sensing device. In situations where known coupling pressures are used, cutaneous blood pressure changes may be referenced to them, as well as to the clinically determined brachial blood pressure.

Since mechanical stability is highly desirable, further stabilization may be achieved by using double-sided adhesive materials between both surfaces of the digit being evaluated where they meet the stabilizing platform and encircling means.

External mechanical shock to the strain gauge is minimized by routing the electrical leads through the platform base where maximum stability is present and placing an all-encompassing cover over the strain gauge assembly. Additionally, shock absorbing materials are placed between the transducer body and its surrounding guide tube.

When the foregoing non-invasive, non-occlusive technique is used as described, it is possible to continuously make cutaneous blood pressure measurements and record patterns under most clinical circumstances and even during strenuous exercise, such as jogging or running on a treadmill.

OBJECTS OF THE INVENTION

In general, it is an object of the present invention to provide a method and apparatus for making measurement of cutaneous blood pressure which will overcome the disadvantages of the prior art.

A further object is to provide a method and apparatus of the above character which does not require immobility of the patient and which provides a continuous, non-invasive blood pressure measurement.

A further object is to provide a method and apparatus of the above character which is so sensitive, it can even record changes in blood pressure due to a smoking cigarette being brought into the presence of a non-smoking person.

It is a further object of the present invention to provide for a non-invasive, non-occlusive blood pressure evaluation technique that will provide permanent records of momentary changes in blood pressure, and make it possible to evaluate even the evanescent effects of interacting neurocirculatory reflexes.

It is yet another object of the present invention to provide a system that is inexpensive to manufacture and easy to use in association with equipment presently widely used by physicians.

These and other objects and features of the invention will become apparent from the following description and claims when taken in conjunction with the accompanying drawings, of which:

BRIEF DESCRIPTION OF THE DRAWINGS

FIG. 1 is a top perspective view of a first embodiment of apparatus for cutaneous blood pressure measuring apparatus.

FIG. 2 is a front view of the apparatus of FIG. 1.

FIG. 3 is a left side view of the apparatus of FIG. 1.

FIG. 8 is another embodiment of the present invention.

FIG. 9 is further embodiment using a calibration system employing a surrounding cuff.

FIG. 10 is a partial cross-sectional view taken along lines 11 of FIG. 9.

DETAILED DESCRIPTION OF THE DRAWINGS

Figure 4:
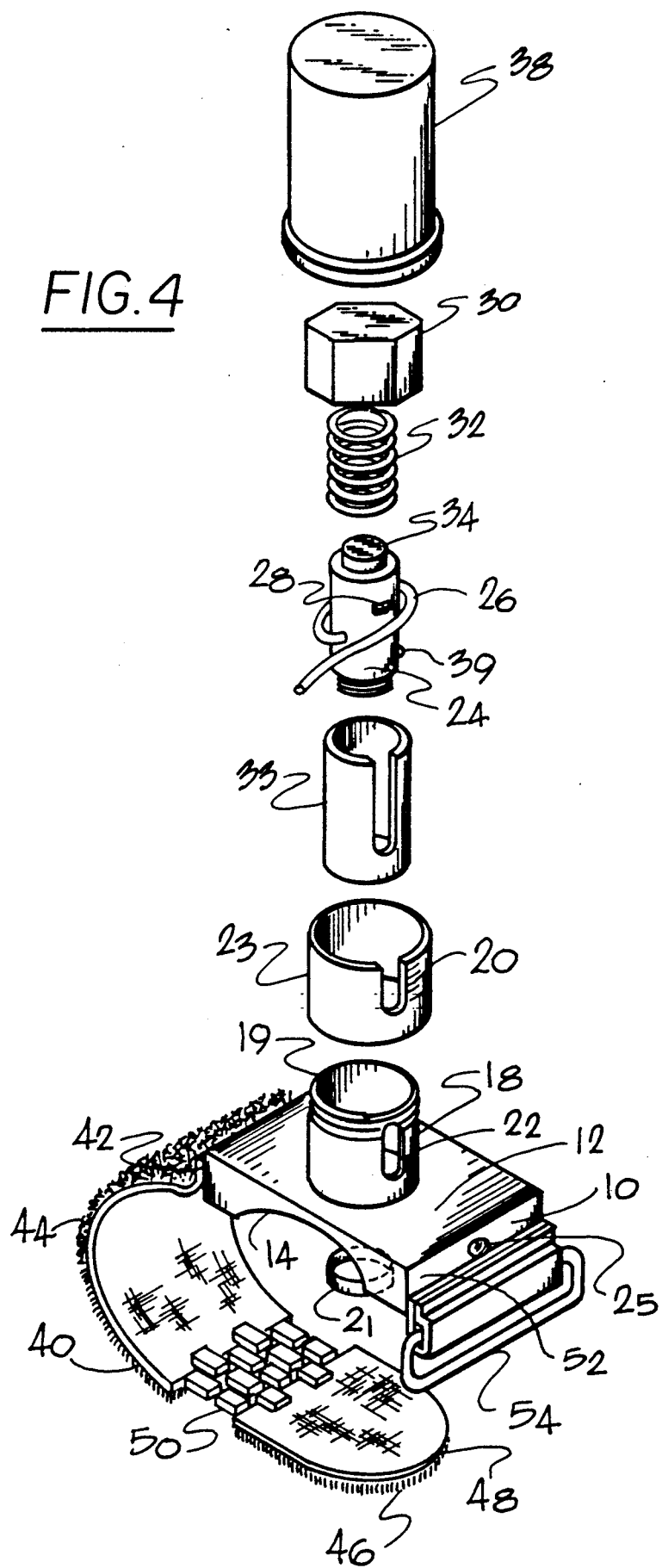
FIG. 4 is an exploded top perspective view of the apparatus of FIG. 1.
Figure 5:
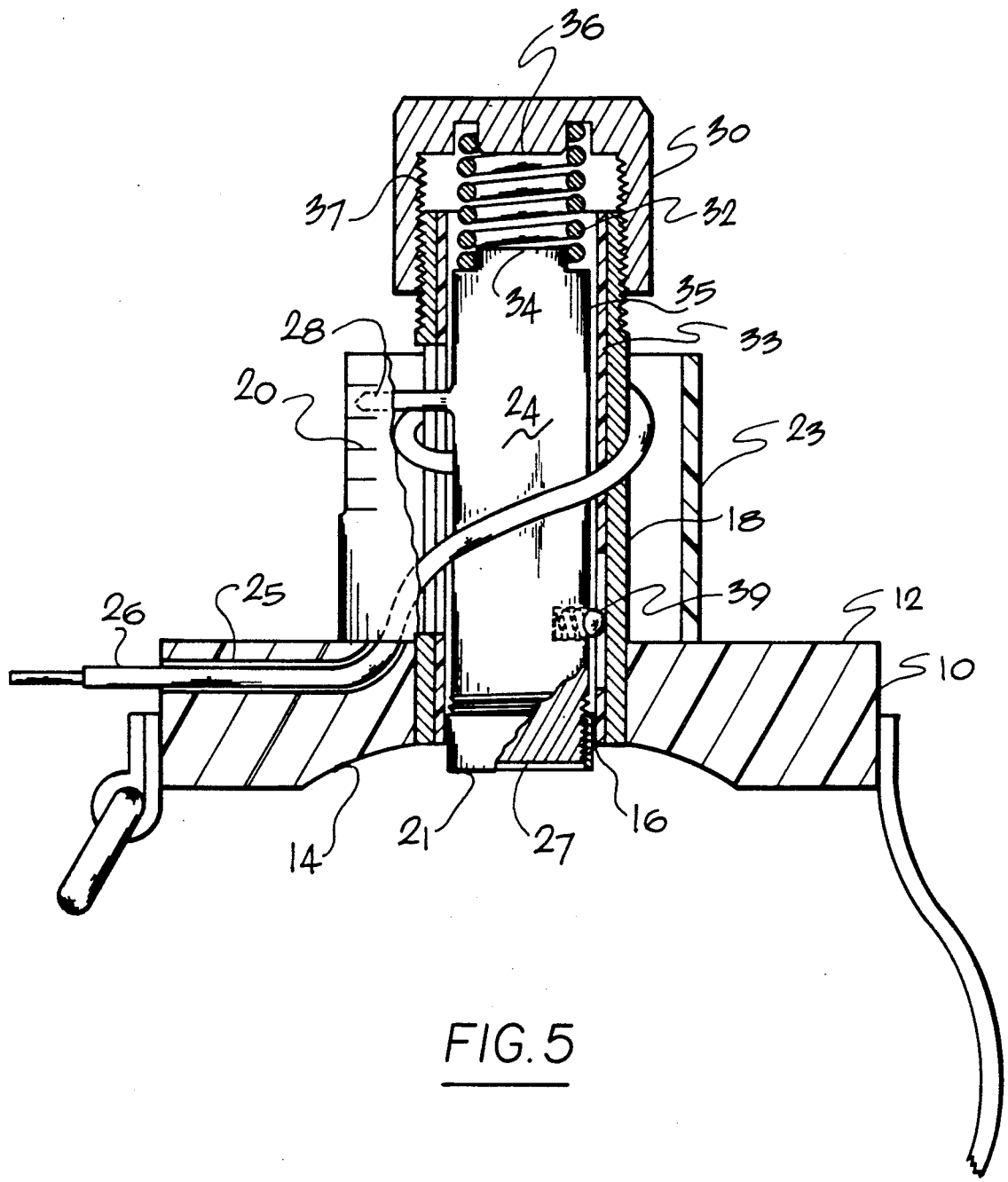
FIG. 5 is a cross-sectional view of a first embodiment of the apparatus of FIG. 1.

Making reference to FIGS. 1 through 5, the first embodiment of the apparatus, adapted for attachment to the thumb, is shown.

A support platform plate 10 has a generally flat rectangular top surface 12 and a concave lower surface portion 14 adapted for conforming to the shape of the fleshy portion of the thumb. Centrally located on support platform 10 is a perpendicularly situated hollow upstanding sleeve 18 having threads 19 at its outer upper end, and extending through the support platform plate to form an opening 16 in the support platform plate 10. Depending below the circumference of the circular opening 16 is an isolation ring 21 that depends slightly below the lower surface portion 14 of the support platform plate.

Within the perpendicular hollow sleeve 18 is fitted a cylindrical pressure measuring transducer or gauge 24 which measures pressure differentials along its longitudinal vertical axis. The pressure measuring transducer 24 fits slidably within shock absorbing and guide sleeve 33 fixed within the internal circumference of the hollow sleeve 18. The diameter of the transducer 24 is approximately ¼", and slightly smaller than the inner diameter of the isolation ring 21. (A marking means 28 is fixed to the external circumference of the transducer.

Electrical lead 26 from the pressure measuring transducer 24 is fitted through a slot 25 in the support platform plate 10 for stability. The electrical lead 26 is connected to a conventional recording device, not shown.

At the upper end 35 of the transducer is a shoulder 34 for holding one end of a coil spring 32, the other end of which is held by an cap shoulder 36 inside cap 30. The cap 30 has internal threads 37 corresponding to the external threads 19 of the perpendicular hollow sleeve 18. The coil spring 32 is thus held between the inside of the cap 30 and the top of the transducer 24 biasing the transducer in a downward direction.

Calibration markings 20 on an outer perpendicular hollow sleeve 23 are used in association with the marking means 28 on the hollow sleeve 18 for setting the tension on the coil spring 32 from the upward force of the thumb on the bottom surface 27 of the transducer 24. The transducer is retained in the hollow sleeve 18 by a detent 39.

The outer perpendicular hollow sleeve 23 may be transparent or have a transparent portion for viewing the marking means 28' directly. As shown in FIG. 2, however, the outer hollow sleeve 23 may have a cut out portion 22 for viewing the marking means 28.

A protective cylindrical cover 38 fits over the cap 30 and hollow sleeve 18 and outer hollow sleeve 23, and is held by a pressure fit against the outer periphery of the hollow sleeve 23.

In the embodiment shown in FIGS. 1 through 5, an inelastic strap 40 is connected to a first side 42 of the lower surface 14 of support platform plate 10. The inelastic strap 40 has on one surface 42 a Velcro loop portion 44, and at the end of the strap 40 on the same side as the Velcro loop portion 44 is a Velcro hook portion 46. Between the Velcro loop portion 44 and Velcro hook portion 46 is a slightly expandable link portion 50. Attached to the other side 52 of the lower surface 14 is an open rectangular portion 54 for receiving the end of the strap 40.

Figures 6, 7:
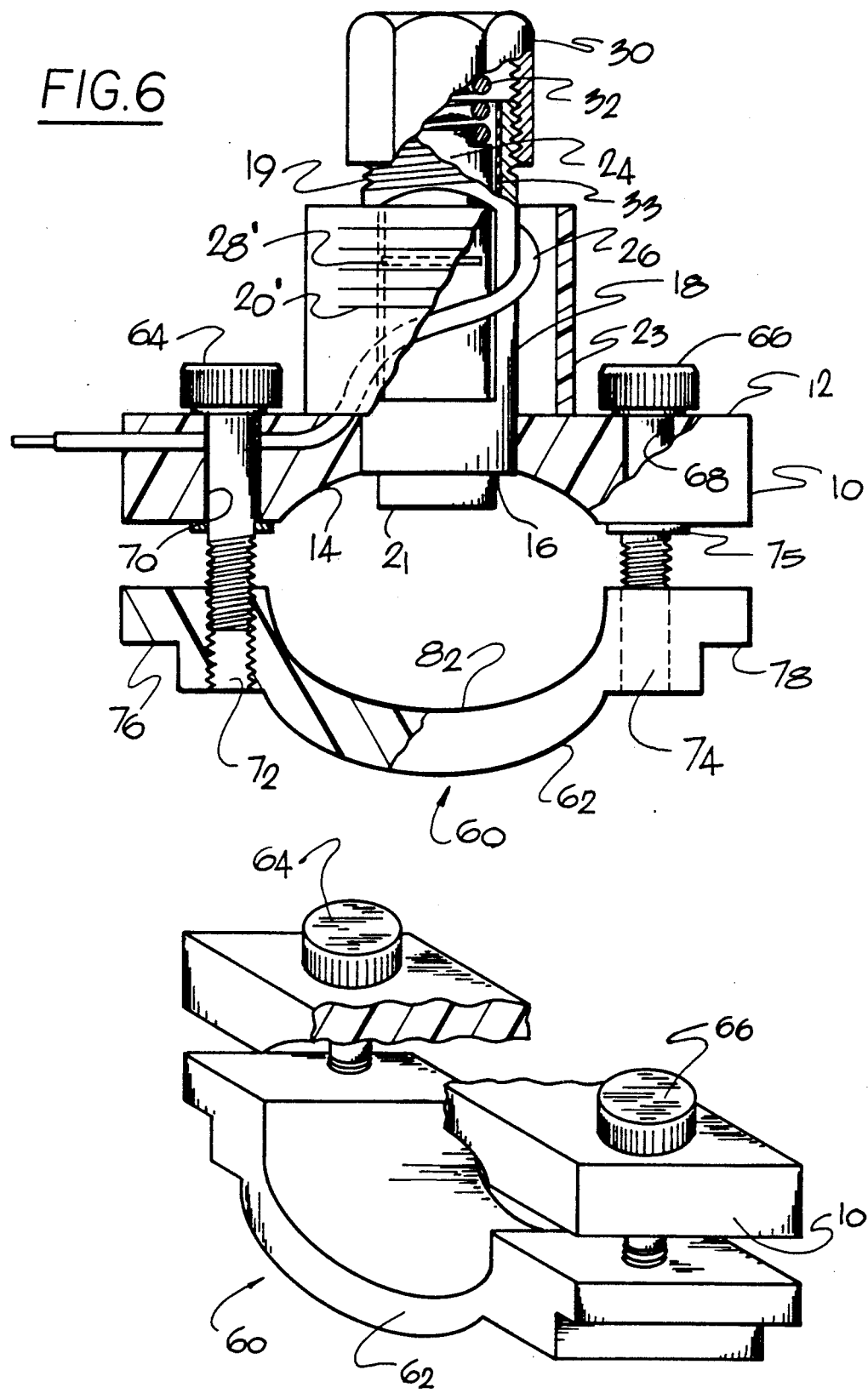
FIG. 6 is a side cross-sectional view of a preferred embodiment of the apparatus for cutaneous blood pressure measuring.
FIG. 7 is a top partial perspective view of the yoke assembly in partial view.

In an alternative embodiment shown in FIG. 6, a rigid yoke 60 is used, in place of the strap 40 shown in FIGS. 1 through 4, to securely attach the apparatus to the thumb. The yoke 60 consists of a semi-circular lower portion 62 of a size and contour to fit the shape of the back of the thumb.

A pair of screws 64 and 66 pass through openings 68 and 70 in the support platform plate 10 into screw holes 72 and 74 in projections 76 and 78 on the sides of the yoke 60. Washers 75 and 77 restrain the screws 64 and 66 from vertical movement.

The operation of the apparatus shown in FIGS. 1 through 4 is as follows: The fleshy portion of the patient's thumb is placed within the concave lower surface portion 14 of the support platform plate 10. The end of the inelastic fabric strap 40 is then passed through the open rectangular portion 54, the end of the strap 48 having the Velcro hook portion 46 is then bent back over itself to come into contact with the Velcro loop portion 44 on the strap 40. Prior to attaching the Velcro hooks 46 to the loops 44, the strap is subjected to tension sufficient to stretch the expandable chain link portion 50 to its maximum extent. With the hook and loop portions 44 and 46 thus connected, the apparatus is substantially fixed in place relative to the thumb.

The isolating ring 21 now has a portion of the fleshy portion of the thumb pushed into the dish formed by the circumference of the ring 21 and the bottom surface 27 of the transducer 24. This isolated tissue is in contact with the lower surface 27 of the pressure measuring transducer 24 biasing it axially upward against the tension of spring 32 at the upper surface of the pressure measuring transducer.

The electrical lead is connected to a conventional strip recorder typically present in a doctor's office for recording the changes in blood pressure of the pressure measuring transducer 24. The cap 30 is then turned until the indicator marking means 28 is approximately at the preferred position, which should be showing the blood pressure reading at approximately 100 mm Hg. The cap 30 would then be placed over the system. Although not as effective, the opening 16 in the support platform plate 10 may serve as an isolation ring, if isolating a portion of cutaneous tissue in the opening. However, to maintain such isolation additional pressure may be required of the thumb against the lower surface 14 of the support platform plate 10 than with the use of the isolation ring 21. The monitor would then provide a record of the pressure variations on the transducer 24 corresponding to the blood pressure in the isolated cutaneous tissue.

As a result of the isolation of the cutaneous tissue, caused by the isolation ring 21, extraneous noise from the remainder of the digit or body itself to the lower surface 27 of the transducer 24 is diminished markedly or eliminated.

In the apparatus shown in FIGS. 6 and 7, the apparatus is used by inserting the thumb in the opening formed between the lower surface of yoke 62 and the concave lower surface 14 of the support platform plate 10. The screws 64 and 66 are then rotated causing the lower portion of the yoke 62 to be pulled towards the concave lower surface 14 trapping the thumb between the two surfaces The screws 64 and 66 are turned until the thumb is securely held in place, but there is no interference with the blood flow to the thumb. The cap 30 is then, turned until the marking means 28 is at the desired position. The remaining operation of the unit is the same as that discussed in FIGS. 1 through 4.

FIGS. 8, 9 and 10 show an embodiment having a transducer fixed in position. The pressure applied to the isolated tissue by the lower surface of transducer is controlled by controlling the pressure generally affixed to the thumb.

In FIG. 8 the isolation ring 21 and the transducer 24 are fixed. The pressure is applied by the thumb to the lower surface 27 of the transducer 24. An expandable air sac 80 is fitted within the concave portion 82 of the lower yoke portion 62. The air sac 80 is inflated by use of a pump ball 84 connected through tube 86 to the air sac 80. A one way valve 88, shown diagramatically.

In operation, the thumb of the patient is inserted in the opening between the air sac 80 and the lower surface 14 of the support platform plate 10. The screws 64 and 66 are then tightened until a pressure meter, connected to the air sac 80 (not shown) reads the desired pressure. Since the pressure of the air sac is the pressure on the thumb, this is also the pressure on the lower surface 27 of the transducer 24.

In FIG. 9 another means of adjusting the initial pressure applied to the transducer 24 is shown. In the embodiment cylindrical pins 90 and 92 have one end fixedly fitted in the support platform and the other end 94 and 96 slidably fitted within openings 98 and 100. The pins 90 and 92 can be fixed within openings 98 and 100 by locking screws 102 and 104. A pressure cuff 106, of a size of the apparatus so that inflation of the cuff covers the compression of the support platform 10 and the yoke 60. Once again the thumb is inserted between the lower surface 14 and the concave surface 82 and the cuff inflated.

When a pressure measuring device for measuring the pressure in the cuff indicates the desired pressure, such as 50 mm Hg then the locking screws 102 and 104 are used to lock the pins 92 and 94 in place.

As indicated previously, the sensitivity of the device is such that the changes in blood pressure to a non-smoker may be measured when someone smoking a cigarette is in close proximity to the non-smoker. Such sensitivity permits obtaining data not previously available. For example, the inventor, Dr. Hon has determined that at the start of passive smoking (Dr. Hon not smoking, but having a cigarette near him), his blood pressure, as determined by the present apparatus was approximately 100 mm of Hg. After approximately seven (7) minutes of being in the presence of smoke his blood pressure rose to approximately 125 mm Hg until after nine (9) minutes his blood pressure was approximately 125 mm Hg of mercury. After the cigarette is removed, Dr. Hon's blood pressure continued to rise until it is approximately 150 mm of mercury two (2) minutes after the cigarette has been removed. His blood pressure remained at approximately 150 mm Hg for about seven (7) more minutes and then continued to rise until it was approximately 165 mm Hg after eleven (11) minutes. The blood pressure thereafter declined steadily, but did not return to approximately normal, until more than eighteen (18) minutes after the removal of the smoke.

This information would not be readily discernable by conventional blood pressure monitoring apparatus even of a continuous nature. Applicant is unaware of any similar direct cardiovascular evidence of the effect of passive smoking. In addition, other detailed cardiovascular effects have been determined showing the effects of various drugs given to a patient during operations or labor. These new data provide detailed cardiovascular evaluation in situations where such an evaluation previously was limited to relatively gross external observations.

The pressure measuring transducer 24 may of a strain gauge type such as are available from Koeningsberg Instruments, Trans America Corporation or Gould, Inc., all of which are responsive to pressure applied to one surface.

While a strain gauge is contemplated as the preferred form of carrying out the present invention it should be realized that many other transducers are available which can measure physiological alterations in the condition of the skin Such conditions may be sensed by resistive elements, by optical indicators, by linear variable differential transformers, by frequency response shifts in resistive capacitance systems (where the transducer is part of the capacitance of a timed circuit), by calibrated springs, by membranes on piezo film and transistors, all of which may be used in the present invention.

It will be apparent to those skilled in the art to which this invention pertains that many adaptions and modifications thereof may be made without departing from its spirit and scope. For example, while the preferred embodiment of the invention has disclosed apparatus for particular applicability to use on the thumb, other sites on the body may be used wherever bony reference points or structures are available so that a stable platform can be established over an adjacent body part without resulting in occlusion of the arterial flow. Examples of such anatomic sites include fingers, toes, the entire forehead including medial, supra-orbital and temporal areas. While each different site may require an individualized stabilizing platform such platform would not depart from the scope and spirit of this invention, as described.

What is claimed is:

1. Apparatus for monitoring blood pressure of a body comprising isolating means for isolating a portion of cutaneous tissue and measuring means for measuring changes in said isolated cutaneous tissue, said isolating means comprising an annular ring.

2. The apparatus of claim 1 in which said measuring means comprises at least one transducer.

3. The apparatus of claim 1 in which said measuring means is a pressure transducer.

4. The apparatus of claim 3 in which said pressure transducer is cylindrical, having an outer diameter substantially that of the inner diameter of the annular ring.

5. Apparatus for monitoring blood pressure of a body comprising:
   a) a support base adapted to be mounted fixed relative to a portion of the body;
   b) means for maintaining said support base fixed relative to said portion of the body;
   c) said support base including means for isolating a portion of cutaneous tissue said isolating means comprising an annular ring adapted to be maintaining against the cutaneous tissue.

6. The apparatus of claim 5 in which said means for maintaining said support base comprises an adjustable substantially inelastic band adapted to encircle a portion of the body.

7. The apparatus of claim 6 in which the means for maintaining said support base is a strap adapted to fit around a digit.

8. The apparatus of claim 5 in which said sensor means comprises a pressure transducer means for sensing changes in pressure in said isolated cutaneous tissue.

9. The apparatus of claim 5 in which said sensor means comprises a laser means for sensing changes in volume of the said cutaneous tissue.

10. A method for monitoring blood pressure of a body comprising the steps of isolating a portion of cutaneous tissue by pressing an annular member on the surface of the skin and measuring changes in the pressure in the cutaneous tissue.

11. The method of claim 10 in which said means for measuring changes in the cutaneous tissue comprises a pressure transducer.

12. The method of claim 10 in which said means for measuring changes in the cutaneous tissue comprises a means for measuring changes in volume of the isolated cutaneous tissue.

13. The method of claim 10 in which said means for isolating a portion of cutaneous tissue is associated with a support base fixed relative to the cutaneous tissue at a portion of the body having a flesh element overlying a rigid structure.

14. The method of claim 13 in which said cutaneous tissue is the fleshy portion of a digit.

15. In a method for measuring blood pressure of a living body with a transducer for sensing a physiological variable which is correlatable with blood pressure, the steps of impressing an annular ring having an open portion lying on a surface against the skin, said open portion defining an orifice into which the skin protrudes when pressed, and mounting the transducer in the orifice in contact with the skin while reading out said physiological variable from said transducer, and calibrating the reading in units related to blood pressure.

* * * * *